United States Patent [19]

Odintsova

[11] 4,310,553

[45] Jan. 12, 1982

[54] PROCESS FOR PRODUCING FOOD VITAMIN CONCENTRATE FROM WINE YEAST

[76] Inventor: Ekaterina N. Odintsova, ulitsa Vavilova, 54, korpus 3, kv. 199, Moscow, U.S.S.R.

[21] Appl. No.: 124,287

[22] Filed: Feb. 25, 1980

[51] Int. Cl.$^3$ .............................................. C12H 1/06
[52] U.S. Cl. ...................................... 426/31; 426/62; 426/72; 435/259
[58] Field of Search ................... 426/60, 656, 311, 72, 426/456, 506, 520, 524, 31, 52, 53, 62, 805; 435/259, 267, 272

[56] References Cited

U.S. PATENT DOCUMENTS

| | | | |
|---|---|---|---|
| 3,961,080 | 6/1976 | Sugimoto et al. | 426/60 |
| 3,975,553 | 8/1976 | Griffon | 426/656 |
| 4,035,517 | 7/1977 | Magny et al. | 426/60 |

FOREIGN PATENT DOCUMENTS

| | | | |
|---|---|---|---|
| 276885 | 6/1967 | U.S.S.R. | 426/60 |
| 521879 | 9/1977 | U.S.S.R. | 426/60 |

*Primary Examiner*—Hiram Bernstein
*Attorney, Agent, or Firm*—Steinberg & Raskin

[57] ABSTRACT

A process for producing food vitamin concentrate from food yeast in which the starting feedstock comprising a by-product from the production of dry wines obtained after separation of a new wine and comprising a residue of the starting strains of wine yeast, highly-tolerant to increased concentrations of the alcohol produced thereby during fermentation, and highly-tolerant to pH of the must below 3.5, with large homogeneous size cells after separation of the remaining wine by pressing and dilution with water in a ratio of 1:1.5–3.0, based on the pressed yeast, is subjected to autolysis; the resulting autolysate is heated to the temperature of 80°–90° C., then cooled to 0°–2° C. and separated from the residue. The recovered autolysate is concentrated to give the desired product.

5 Claims, No Drawings

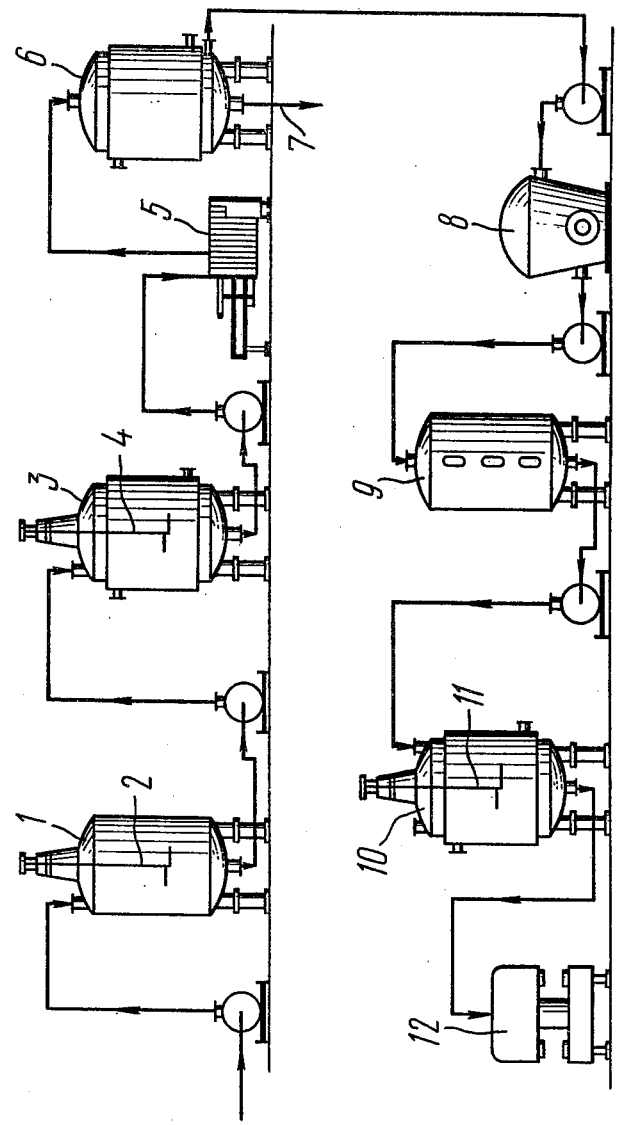

PROCESS FOR PRODUCING FOOD VITAMIN CONCENTRATE FROM WINE YEAST

The present invention relates to the art of yeast microbiology and vitaminology and, more specifically, relates to a process for producing a food vitamin concentrate from food yeast.

FIELD OF THE INVENTION

The vitamin concentrate from food yeast according to the present invention is useful as an additive to various food products for enriching the same with vitamins of group B, aminoacids and trace elements; furthermore, the concentrate according to the present invention can be used as such as a food stuff product and it may be administered per os in the case of shortage of vitamins of group B in the organism of human beings and animals and after cavitary operations when it is necessary to administer a residue-free food; it is also useful in agriculture as a fertilizer.

BACKGROUND OF THE INVENTION

Among currently known food yeast employed as a man's additional foodstuff there are beer yeast and pressed baker yeast. These are saccharomycetes ("sugar fungi") capable of initiating an intensive alcoholic fermentation.

Pressed baker yeast cannot be obtained in amounts sufficient for use thereof as food yeast. There is usually a certain shortage of the yeast to satisfy the demand in their direct application—manufacture of yeast flour products. Furthermore, the yeast contain only minor amount of vitamin $B_1$ which is vitally important in human metabolism. Thus, pressed baker yeast contain in one gram of dry solids only about 1 microgram of vitamin $B_1$, very rarely—up to 10 μg; beer yeast—up to 200 μg/g of dry solids.

Employed for nutrition purposes are liquid and dry beer yeast. The resources of beer yeast for food purposes are rather scarce. The reason is that in the manufacture of beer the amount of yeast accumulation upon fermentation of malt must is consumed for the next cycle of fermentation and so on until they lose their force and become enriched with contaminating lactic-acid bacteria undesirable for brewing. Employed for the food purposes are waste yeast with a certain amount of weakened and autolyzable yeast cells. In addition, they contain a small amount of lactic-acid bacteria equally useful. Therefore, the liquid portion contains a certain, and in some cases even considerable, amount of physiologically active compounds. However, totally viable yeast cells, due to a very dense shell thereof, cannot be cleaved in a human stomach and pass through the intestine in their unchanged form.

Known in the art is a process for producing a food vitamin concentrate from beer yeast by carrying out autolysis thereof. The autolysis is preceded by a treatment (washing) of yeast with an alkali solution to eliminate bitter taste. A separator is employed for separation of the residue. The autolysis is conducted at a temperature of from 45° to 50° C. The best results in the yield of nitrogen-containing matters are obtained at the autolysis temperature of 45° C. The resulting autolysate is subjected to a further heating to a temperature of 80° C. Then the autolysate is exempted from cell shells by means of a separator. The resulting transparent autolysate is additionally filtered through a bacterial laminar filter to remove occasional bacteria present in the filtrate. The concentration is conducted in a centrifugal thin-layer evaporator. The required temperature and pressure are determined on the basis of retention of thiamine in the autolysate upon thickening thereof. The final stage, i.e. drying, is conducted at a temperature of 80° C. by means of spraying. In this process losses of thiamine vary from 10 to 20%. The final product has a pleasant odour and contains amino acids in the amount of 480 mg/g. (E. Pajunen, E. Pessa, M. Linko. Production of yeast extract from waste brewery yeast. Third Intern. Specialized Sympos. on Yeasts. Proceedings. Otaniemi-Helsinki. Finland, 1973, Part I, Abstracts, p.91).

This process requires a great amount of the starting feedstock, i.e. brewery yeast, scarcity of which yeast hinders the industrial production of a vitamin concentrate on their basis. The category of alimentary or food yeast should be also exemplified by wine yeast in the production of dry wines.

The production of a food vitamin concentrate from wine yeast resulting from the production of dry wines is novel and hitherto unknown from the literature.

BRIEF SUMMARY OF THE INVENTION

It is an object of the present invention to provide a process which makes it possible to produce a food vitamin concentrate enriched with vitamins of group B, aminoacids and trace elements.

It is another object of the present invention to enlarge the range of raw materials for the production of a food vitamin concentrate by making use of the by-product resulting from the production of dry wines.

It is still another object of the present invention to perform the process for the production of a food vitamin concentrate simultaneously with retaining and utilizing the residue of salts of tartaric acid.

The main and other objects are accomplished by a process for the production of a food vitamin concentrate from food yeast involving autolysis of the starting stock, separation of the resulting autolysate from the residue and concentration thereof, in accordance with the present invention as the starting stock use is made of a by-product resulting from the production of dry wines obtained after separation of new wine and comprising the residue from the starting strains of wine yeast highly tolerant to increased concentrations of the alcohol formed thereby in the fermentation process and to pH values of the must below 3.5 with large homogeneous size of cells; the starting feedstock after the separation of the wine residue by way of pressing and dilution with water in a ratio of 1:1.5-3.0 based on the pressed yeast is subjected to autolysis; the resulting autolysate is heated to a temperature within the range of from 80° to 90° C., then cooled to a temperature of about 0° to 2° C. and the autolysate is separated from the residue; the isolated autolysate is concentrated to the desired product.

It is advisable that the autolysis be conducted at a temperature within the range of from 44° to 48° C. for a period amounting to 1.5-3 days. Autolysis can be also conducted at a temperature of from 8° to 12° C. for a period of from 5 to 8 months. The recovered autolysate is concentrated to 45-50% residual moisture or, after concentration to the above-specified residual moisture, it is subjected to lyophilic drying to a dry state. The final concentrate is in the form of either a thick dark-brown paste or a dry powder.

DETAILED DESCRIPTION OF THE INVENTION

As the new source for the preparation of the food vitamin concentrate according to the present invention use is made of wine yeast from the production of dry grape wines. It is also possible to use yeast from the production of dry fruit wines. In the second case the starting feedstock contains a smaller amount of vitamins of group B. Consequently, the yeast accumulated in fermentation of this latter feedstock are not so enriched with vitamins of group B: the content of vitamins of this group is the result of accumulation thereof by the yeast cells at the end of fermentation.

Grapes and, consequently, grape juice and must, are rich in the content of vitamins of Group B—inositol, biotin, pantothenic acid, vitamin $B_1$ (thiamin), vitamin $B_2$ (riboflavin), vitamin $B_6$ (pyridoxine), vitamin PP (nicotinic acid), folic acid and its active component, viz. para-aminobenzoic acid.

By the end of must fermentation almost all the amount of these vitamins is taken-off by the yeast cells which use it as a stock. Therefore, the residual yeast from the production of dry grape wines are enriched with said vitamins of group B. They also contain trace elements and a considerable amount of protein substances. As to the nutritive value, the latter substances rank second after meat. However, all the valuable contents of cells of the residual wine yeast from the production of dry grape wines are discarded: the residue as a whole i.e., yeast and tartrates precipitated therewith, are used currently in the world only for the production of tartaric acid.

The recovery of physiologically active substances from the starting feedstock is effected by the conventional method of cell autolysis; however, the process is conducted with retaining tartrates in the residue along with empty shells of the yeast cells which tartrates are precipitated together with the fermented yeast cells. Tartrates comprise the sole source for the production of tartaric acid per se. In further processing, after separation of the autolysate from the salt precipitate, the latter is utilized. For autolysis use may be made of wine residual yeast, i.e. so-called liquid yeast (after decantation of new wine they can contain a small amount of this wine). As to their consistence, they comprise a thick mass with the content of dry substances of 10%.

The starting feedstock prior to autolysis is subjected to pressing, followed by dilution with water.

This dilution of the pressed material with water is effected in a ratio of 1:1.5–3.0 based on the pressed yeast. The lower limit of this ratio is slightly lower than the theoretical one (1:2.5) due to the fact that during the first 6 hours the process of autolysis occurs very intensively with a rapid accumulation of water-soluble aminoacids thus facilitating a rapid liquefaction of the mixture and the further autolysis proceeds at an optimal ratio between the liquid and solid phases.

At a temperature within the range of from 44° to 48° C. the duration of autolysis is 1.5 to 3 days.

Autolysis of this liquid yeast may be conducted at a lower temperature of from 8° to 12° C. In this case the autolysis duration is as long as 5 to 8 months.

The temperature range of from 44° to 48° C. is selected taking into account the fact that at the temperature of 50° C. the activation of proteolytic enzymes, which perish at the temperature of 51° C., starts. For this reason, it is dangerous to conduct autolysis at a temperature above 48° C. However, the lower limit of temperature below 44° C. is also undesirable.

The autolysis of cells of the residual wine yeast will occur most intensively where the yeast are separated from wine by pressing (the content of the yeast in the whole residue is 1% on the average), washed with potable water, again pressed; washings are used for recovery of the alcohol while the yeast are diluted either with potable water or with a distillate. The maximum ratio is 1:3, minimum 1:1.5 based on the pressed yeast.

Under these conditions the autolysis duration is reduced to 36 hours. The autolysis duration at a temperature of from 8° to 12° C. is reduced to 5 months. On completion of autolysis the autolysate is obligatorily heated along with the total of the residue to a temperature of 80° to 90° C. This stipulates mainly a more complete recovery of substances from the yeast cell and coagulation of the residual amount of protein substances (according to Abderhaldem in the enzymatic hydrolysis 95% of proteins is split). The coagulation of the residual protein contributes to a subsequent precipitation of the residue. Upon heating tartrates remain in dissolved condition.

A further stage following the heating comprises cooling to a temperature of from 0° to 2° C. to crystallize and precipitate tartrates. The transition of tartrates into the crystalline state at a temperature about zero is effected very rapidly. During precipitation of the tartrates empty shells of the yeast cells coagulate only insignificantly. Completeness of precipitation of the tratrates is determined by chemical analysis.

After precipitation of tartaric acid salts the opaque autolysate is decanted into an intermediate vessel.

A further removal of empty shells of the yeast cells may be conducted in two ways: either centrifugation or keeping in vessels at a temperature of from 0° to 2° C. for a period of up to 1.5 months.

Concentration of the autolysate should be preferably conducted at the minimum possible temperature in a vacuum apparatus. It is advisable to use temperature of from 45° to 50° C. at a reduced pressure but not more than 70° C. Vitamins of group B are not decomposed in an acidic medium.

The concentrated autolysate with a moisture content of 45 to 50% may be added, in the required concentrations, with three vitamins of group B: vitamin $B_{12}$ which is absent in the yeast and grapes; vitamin $B_{15}$ (pangamic acid), orotic acid.

The final concentrate is stored in sealed tin cans of 2, 3 and 10 kg. Dispensing of low doses in tubes is also provided.

The dry preparation is obtained by drying the concentrate at a temperature of −40° C. The commercial form of a dry preparation comprises gelating capsules with 0.5 g of the preparation in each. The food vitamin concentrate is of a dark-chocolate colour and sour taste.

For a better understanding of the present invention, some specific Examples illustrating the process are given hereinbelow.

EXAMPLE 1

1.5 ton of the residue obtained after separation of new grape wine containing biomass of the starting yeast strain of *Saccharomyces vini* (ellipsoideus) and salts of tartaric acid with the content of dry solids of 10% are subjected to pressing, then washed with water and pressed again. The washing water is used for recovering the alcohol. The pressed mass (with the content of pressed yeast of 1%) is diluted with potable water in the ratio of 1:2 based on the pressed yeast and subjected to autolysis at the temperature of 45° C. for 36 hours under continuous stirring in an enameled tank provided with a jacket for passing water heated to the required temperature and with a stirrer. On completion of the autolysis the material along with the residue is heated to the temperature of 80° C. to ensure a more complete recovery of the substances from the yeast cells. The heating is conducted in the same tank.

During the autolysis and subsequent heating of the autolysate and the residue, the tartrates are in dissolved condition. That is why the following stage comprises cooling of the material to crystallize the salts of tartaric acid and precipitate them. To do so, after heating of the material, i.e. autolysate with the residue, it is placed into an enameled tank provided with a jacket through which a cooling mixture at a temperature of 0° to 2° C. is passed. The tartrates are crystallized and precipitated. The absence of tartaric acid in the liquid above the residue is controlled automatically. This mixture is maintained for a period of one week.

After precipitation of tartaric acid salts the liquid above the residue (autolysate) is decanted. There are obtained 2,500 kg of the autolysate. The precipitate is then delivered to isolation of tartaric acid. Empty shells of the yeast cells slowly settle and the main portion thereof remains in the decanted autolysate. The autolysate is centrifuged at a speed of 6,000 r.p.m. for 10 minutes and the residue comprising cell shells is separated. There are obtained 2,400 kg of a transparent autolysate. Then the autolysate is concentrated in a vacuum apparatus at a temperature from 70° to 80° C. The concentrated autolysate with the moisture content of 50% in the amount of 1,200 kg is poured into an enameled vessel and into the still hot concentrate, the following vitamins of group B are added, each in the form of a concentrated aqueous solution: 360 g of orotic acid, 12 g of pangamic acid (vitamin $B_{15}$) and 12 g of vitamin $B_{12}$. Thereafter it is packed into tin cans with a capacity of 3 and 10 liters.

The resulting concentrate contains vitamins of group B, 17 aminoacids and various trace elements. The content of vitamins, aminoacids and trace elements in the thus-produced food vitamin concentrate is given in the following Tables 1, 2 and 3. Shown in Table 1 is the content of vitamins of group B in 10 g of the concentrate according to the present invention in comparison with the content of these vitamins in the entire volume of a man's blood (normal)—5 liters.

EXAMPLE 2

The process is conducted in a manner similar to that described in the foregoing Example 1. The resulting final concentrate in the amount of 1,200 kg containing 50% of the residual moisture and having a composition similar to that described in Example 1 is dried at a temperature of 40° C. to the dry state (residual moisture of 1%). There are obtained 606 kg of a dark-brown powder which is packed into gelatine capsules of 0.5 g each.

TABLE 1

Content of vitamins of group B in: man's blood (normal) and in the concentrate according to the present invention

| Vitamins | Blood µg/ml | Blood mg/5 l | Concentrate of autolyzate µg/ml | Concentrate of autolyzate µg/10 ml |
|---|---|---|---|---|
| Meso-inositol | 15 | 75 | 6,376 | 64 |
| Biotin | 0.006 | 0.03 | 4.48 | 0.05 |
| Pantothenic acid (Vitamin $B_3$) | 1.000 | 5.00 | 128 | 3.00 |
| Thiamine (Vitamin $B_1$) | 0.3 | 1.5 | 64 | 0.64 |
| Pyridoxine (Vitamin $B_6$) | 0.06 | 0.3 | 64 | 0.64 |
| Riboflavin (Vitamin $B_2$) | | | 64 | 0.64 |
| Nicotinic acid | 15.00 | 75.00 | 383 | 4.00 |
| Para-aminobenzoic acid | 0.02 | 0.1 | | |
| Folic acid | | | 2.20 | 0.02 |
| Vitamin $B_{12}$ | 0.02 | 0.1 | 10.00 | 0.10 |
| Vitamin $B_{15}$ | | | 10.00 | 0.10 |
| Orotic acid | | | 128.00 | 3.00 |

TABLE 2

Content of aminoacids in the concentrate according to the present invention

| Aminoacid | Content of aminoacid with 50% moisture mg/g | Content of aminoacid with 50% moisture mg/10 g |
|---|---|---|
| Lysine | 4.77 | 47.7 |
| Histidine | 6.69 | 66.9 |
| Arginine | 5.83 | 58.3 |
| Aspartic acid | 8.64 | 86.4 |
| Threonine | 2.84 | 28.4 |
| Serine | 3.74 | 37.4 |
| Glutamic acid | 2.08 | 20.8 |
| Proline | 9.33 | 93.3 |
| Clycine | 2.48 | 24.8 |
| Alanine | 9.22 | 92.2 |
| Valine | 4.56 | 45.6 |
| Methionine | 2.08 | 20.8 |
| Iso-leucine | 2.75 | 27.5 |
| Leucine | 6.79 | 67.9 |
| Tyrosine | 2.86 | 28.6 |
| Phenyl-alanine | 4.20 | 42.0 |
| Aminobutyric acid | 3.85 | 38.5 |
| Total | 82.70 | 827.0 |

TABLE 3

Content of trace elements in the concentrate according to the present invention

| Trace element | Content of trace element 50% humidity, mg/g | Content of trace element 50% humidity, mg/10 g |
|---|---|---|
| Iron | 2.3 | 23 |
| Magnesium | 3.16 | 31.6 |
| Calcium | 2.41 | 24.1 |
| Phosphorus | 2.9 | 29.0 |
| Potassium | 2.5 | 25.0 |
| Sodium | 1.67 | 16.7 |
| Aluminium | 0.24 | 2.4 |
| Boron | 0.23 | 2.3 |
| Manganese | 0.063 | 0.63 |
| Zinc | 0.035 | 0.35 |
| Strontium | 0.025 | 0.25 |
| Tin | 0.009 | 0.09 |
| Silicium | 0.042 | 0.42 |
| Lead | 0.0029 | 0.029 |
| Chromium | 0.015 | 0.15 |
| Titanium | 0.0009 | 0.009 |
| Nickel | 0.005 | 0.05 |
| Cobalt | 0.0015 | 0.015 |
| Molybdenum | 0.00012 | 0.0012 |

TABLE 3-continued

Content of trace elements in the concentrate according to the present invention

| Trace element | Content of trace element 50% humidity, | |
|---|---|---|
| | mg/g | mg/10 g |
| Copper | 0.0035 | 0.035 |

EXAMPLE 3

400 kg of a residue with a content of ingredients similar to that described in Example 1 hereinbefore are subjected to pressing, followed by washing with water and pressing. The washing water is employed for recovery of the alcohol. The pressed mass (with the content of pressed yeast of 1%) is diluted with potable water in the ratio of 1:1.5 based on pressed yeast and subjected to autolysis at a temperature of 10° C. for 5 months under continuous stirring in an enameled tank without any jacket. On completion of the autolysis, the material along with the residue is heated to a temperature of 90° C. in the same tank by passing dry steam under continuous stirring. Further steps of the process are performed as described in Example 1 hereinbefore. There are obtained 220 kg of a concentrate with a residual moisture content of 45%; it comprises a dark-brown paste with a content of vitamins of group B, aminoacids and trace elements similar to corresponding values specified in Example 1.

What is claimed is:

1. A process for producing a food vitamin concentrate from food yeast, which comprises subjecting to autolysis a feedstock composed of the by-product of the production of dry wines obtained after separation of new wine and comprising a residue of the starting strains of wine yeast highly-tolerant to increased concentrations of the alcohol produced thereby during fermentation and highly-tolerant to pH of the must below 3.5, said yeast having large homogeneous size cells, after separation of the remaining wine by pressing and dilution with water in a ratio of 1:1.5 to 1:3.0 based on pressed yeast; heating the thus obtained autolysate to a temperature of from 80° to 90° C.; cooling the same to a temperature of from 0° to 2° C.; separating the autolysate from the residue; and concentrating the recovered autolysate to thus obtain a food vitamin concentrate.

2. A process as claimed in claim 1, wherein said autolysis is conducted at a temperature of from 44° to 48° C. for a period of from 1.5 to 3 days.

3. A process as claimed in claim 1, wherein said autolysis is conducted at a temperature of from 8° to 12° C. for a period of from 5 to 8 months.

4. A process as claimed in claim 1, wherein the recovered autolysate is concentrated to 45–50% residual moisture.

5. A process as claimed in claim 4, wherein the concentrated autolysate is subjected to lyophilic drying to dry state.

* * * * *